(12) United States Patent
Seriwala

(10) Patent No.: US 6,521,201 B1
(45) Date of Patent: Feb. 18, 2003

(54) PROCESS FOR RECOVERY OF HIGH PURITY HYDROPHILIC SULFUR

(75) Inventor: Mohammed Munaf Seriwala, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 129 days.

(21) Appl. No.: 09/782,230

(22) Filed: Feb. 14, 2001

(51) Int. Cl.[7] ............................................. C01B 17/04
(52) U.S. Cl. ........................ 423/567.1; 423/242.1; 423/571; 423/573.1; 423/576.2; 423/576.4; 423/DIG. 17; 435/168; 435/170; 210/601; 210/620; 210/622
(58) Field of Search ................... 423/567.1, 571, 423/573.1, 576.4, DIG. 17, 242.1, 576.2; 435/168, 170; 210/601, 620, 622

(56) References Cited

U.S. PATENT DOCUMENTS

| | | | |
|---|---|---|---|
| 4,243,648 A | * 1/1981 | Fenton | 423/573 R |
| 4,269,699 A | * 5/1981 | McCready et al. | 75/101 R |
| 4,393,037 A | * 7/1983 | Delaney et al. | 423/573 R |
| 5,354,545 A | 10/1994 | Buisman | 423/242.1 |
| 5,518,519 A | 5/1996 | Kondoh et al. | 75/231 |
| 5,637,220 A | 6/1997 | Buisman | 210/605 |
| 5,976,868 A | * 11/1999 | Buisman | 435/266 |
| 6,051,518 A | 4/2000 | Srivastava et al. | 502/20 |

FOREIGN PATENT DOCUMENTS

JP    6-287649 A    * 10/1994    ......... 423/DIG. 17

* cited by examiner

Primary Examiner—Stanley S. Silverman
Assistant Examiner—Timothy C. Vanoy
(74) Attorney, Agent, or Firm—John G. Tolomei; Frank S. Molinaro; Arthur E. Gooding

(57) ABSTRACT

High quality hydrophilic sulfur is recovered from a biologial conversion zone in which a sulfur containing compound such as a sulfide is converted to elemental sulfur. The sulfur is rendered hydrophilic due to the fine particle size and attachment of biomass to the particles. The sulfur is recovered as an undamaged agglomerate powder after being processed in at least two stages of purification.

6 Claims, 1 Drawing Sheet

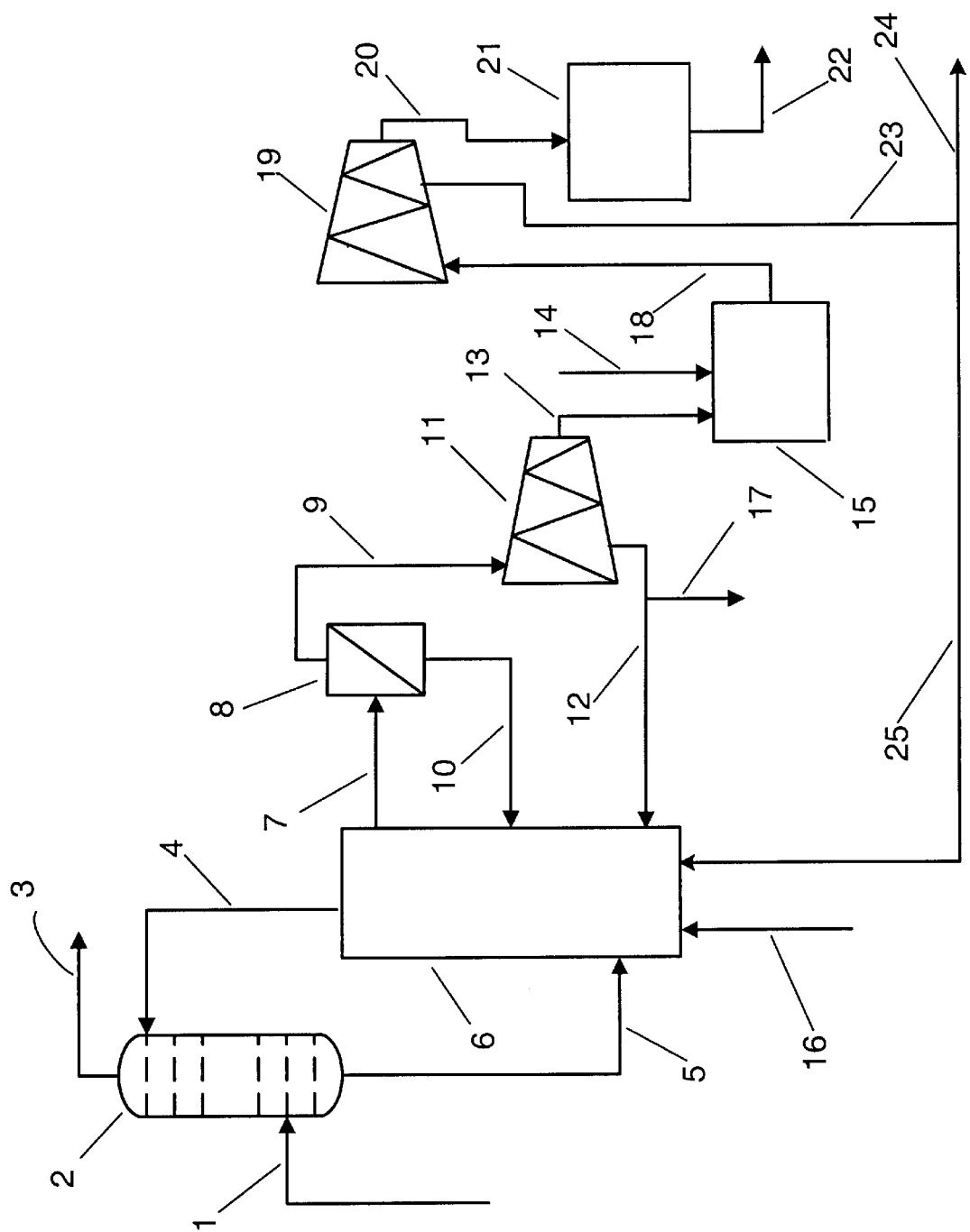

PROCESS FOR RECOVERY OF HIGH PURITY HYDROPHILIC SULFUR

FIELD OF THE INVENTION

The invention relates to a process for the purification and recovery of particulate sulfur from a biological process for converting sulfur compounds. The invention more specifically relates to a sulfur recovery method which produces fine particle high purity sulfur retaining a selected amount of attached biomass which imparts hydrophilic properties to the sulfur.

RELATED ART

A number of processes have been developed to biologically reduce the concentration of a sulfur compound in process streams involved in petroleum refining or other industrial processes. Many of these processes are directed toward reducing the concentration of sulfur compounds present in aqueous streams used to remove sulfur compounds from a flue gas or process stream. These aqueous streams are passed into a biological reaction zone in which a bacteria converts the sulfur compound into elemental sulfur. This is shown for instance in U.S. Pat. Nos. 5,354,545 and 5,518,519 issued to C. J. N. Buisman. The second patent shows the treatment of a gas stream in a scrubber with aqueous liquid which is biologically regenerated and returned to the scrubber. Sulfur is recovered via a settling zone.

U.S. Pat. No. 5,637,220 also issued to C. J. N. Buisman illustrates a reactor for use in biological conversions. The patent points out that the biological agent can be part of a film on various carriers including particulate sulfur produced in the process.

U.S. Pat. No. 6,051,518 issued to K. C. Srivastava presents a microbial process for the regeneration of solid sulfide-containing catalysts. The patent includes a description of the LO-CAT® process, which is described as a prior art liquid redox process. The depiction of this process shows sulfur recovered from an aerobic reactor being pumped to a belt filter. Sulfur from this filter is them passed into a reslurry vessel and the slurry is passed into a separator. The sulfur is eventually melted and stored.

BRIEF SUMMARY OF THE INVENTION

The invention is a method for recovering high purity small diameter particles of elemental sulfur having sufficient attached biomass to impart hydrophilic properties to the sulfur from a biological treatment process.

One broad embodiment of the invention may be characterized as a biological process for conversion of sulfur compounds to elemental sulfur and the recovery of a hydrophilic fine particle sulfur product, which process comprises passing an aqueous stream containing a sulfur compound into a biological reaction zone in which the sulfur compound is brought into contact with a bacteria at conversion promoting conditions under which the bacteria extracts sulfur from the sulfur compound, thereby forming elemental sulfur; removing a reactor effluent stream comprising water, biomass, particles of elemental sulfur and salts from the biological conversion zone and passing the reactor effluent stream into a separation zone in which water and biomass are separated from the reactor effluent stream to yield a separator effluent stream comprising particulate elemental sulfur and water; passing the separator effluent stream into a first centrifugal separation zone and removing water to yield a second separation zone effluent stream containing over about 50 wt % particulate elemental sulfur having attached biomass; admixing the second separation zone effluent stream with water to form a slurry containing less than about 15 wt % solids; passing the slurry into a second centrifugal separation zone and removing water to yield a third separation zone effluent stream containing over 50 wt % particulate elemental sulfur having attached biomass; drying the third separation zone effluent stream to yield agglomerated hydrophilic fine particle elemental sulfur which contains attached biomass.

BRIEF SUMMARY OF THE DRAWING

The drawing is a simplified flow diagram of a process in which the gas stream of line 1 is scrubbed, the scrubbing solution is regenerated in bioreaction zone 6 and fine particles of elemental sulfur are recovered via line 22.

DETAILED DESCRIPTION AND PREFERRED EMBODIMENTS

The biological conversion of sulfur compounds has been investigated for its utility in treating aqueous streams containing undesired sulfur compounds. The aqueous stream may be one which is circulated through a process as a scrubbing or treating solution or the aqueous stream may itself be a process or product stream of another operating unit. The biological conversion may employ either aerobic or anaerobic bacteria or both in sequential reaction zones. During the biological conversion the bacteria removes sulfur atoms from sulfur-containing organic or inorganic molecules or ions of the feed. Not all sulfur-containing molecules may be susceptible to biological conversion, and the this will vary with the molecule. Which feed molecules are acted upon normally depends on the bacteria and conditions. The usual product of this bacterial action is some form of elemental sulfur. The sulfur is then separated from the aqueous reaction media of the biological conversion zone and recovered as a product.

The subject invention is directed to the steps used in recovering the sulfur produced in these processes in its original form without conversion or change in form as by melting and filtration. The reason for this is that the very fine particulate sulfur which can be recovered from these processes can have desirable characteristics, such as of being hydrophilic. A fine hydrophilic sulfur has utility as a sprayable insecticide or plant protectorant. It is believed the hydrophilic nature of the sulfur is caused by the sulfur particles having a definite content of attached biomass and a very fine particle size. The requirements of retaining these characteristics combine to eliminate some fundamental separation techniques, such as belt filtration and melting. For instance, belt filtration appears to be unsuitable for this process as the biomass present in the sulfur slurry tends to "blind" or clog filters. This can also be a problem with some types of centrifuges. Melting and filtration of the liquid sulfur removes the attached biomass believed at least partially responsible for the hydrophilic nature of the fine particles.

It is an objective of the subject process to provide an improved process for the recovery of particulate elemental sulfur from biological reaction zones. It is a specific objective of the invention to provide a process for the recovery of hydrophilic sulfur particles from a biological conversion zone.

The subject invention achieves these objectives by the use of a unique separatory flow scheme that provides high purity (greater than 99 wt % dry basis) sulfur which retains it original fine particle size and a limited but definite coating of attached biomass.

The overall process flow of the subject invention can be best described by reference to the Drawing. The Drawing is a simplified flow diagram of the preferred embodiment of the invention, in which the gas feed stream of line 1, which comprises a sulfur compound, such as hydrogen sulfide, is passed into a lower portion of a scrubbing column 2. In the scrubbing column the ascending gas feed stream is brought into contact with a stream of mildly alkaline aqueous liquid fed to the scrubbing column through line 4. The contact between these two streams results in the transfer of the acidic hydrogen sulfide to the aqueous phase, which is removed from the scrubbing column 2 via line 5. The treated gas feed stream leaves the scrubbing column through line 3.

The "rich" aqueous stream formed in this manner is passed into a biological reaction zone 6 wherein it is admixed with a suitable bacteria maintained at biological conversion conditions. The type of reactor and the conditions within the reaction zone will be governed to a large extent by whether an aerobic or anaerobic conversion is performed. An aerobic conversion is preferred, and air is charged to the reactor 6 via line 16. The residual nitrogen and other gases are vented from the reactor by a line not shown. Also not shown are lines for nutrient and carbonate solution addition. The result of the process is the conversion of the sulfur species carried by the aqueous liquid into elemental sulfur. A watery slurry of elemental sulfur and biomass is removed from the reactor 6 via line 7 and passed into a first separator 8 in which much of the free liquid and biomass is separated from the slurry. The recovered liquid is returned to the reactor 6 via line 10 to return the water, salts and biomass to the reactor. This produces a slurry of about 10% sulfur which is carried by line 9 into a solid bowl first centrifuge 11. This type of centrifuge is preferred as it will not be blinded by the biomass. The action of the first centrifuge produces a cake of about 60% sulfur which is removed via line 13 and a liquid stream of line 12. The liquid is returned to the reaction zone 6 through line 12, with a small amount being bled off the process as waste water through line 17 as needed to balance the salt concentration, etc. in the reaction zone. The amount of attached biomass on the sulfur particles entering and leaving the centrifuge 11 is approximately the same, but free biomass, sulfates, sodium and water in the centrifuge solids stream are greatly reduced.

The solids cake of line 13 is admixed with demineralized water from line 14 and passed into a reslurry vessel 15 in which the cake and water are admixed to a uniform consistency to provide a new slurry of about 10 wt % sulfur. The sulfur in this new slurry will still contain attached biomass and is passed via line 18 into a second centrifuge 19. The second centrifuge removes water to produce a second cake of about 60% sulfur, with the sulfur still containing attached biomass. The second cake is removed via line 20 and contains about 99 wt % sulfur on a dry basis. It is passed into a dryer 21 which produces the final particulate elemental sulfur removed from the process via line 22. The liquid removed from the slurry is withdrawn from the second centrifuge through line 23. A portion of this liquid may be withdrawn via line 24 if desired to maintain desired conditions in the reaction zone, but the majority of the liquid is returned to the reaction zone 6 via line 25.

This depiction of the process has been simplified by elimination of many pieces of equipment of a customary nature such as motors, pumps, solids transfer equipment, control systems and valves, and other process instrumentation. This equipment may be of a conventional nature for this type of process.

The product sulfur produced by the process should be of high purity, which is intended to indicate it contains in excess of 99% sulfur by weight. Part of the non-sulfur portion of the product is the attached biomass which is believed necessary to impart the desired hydrophilic properties to the sulfur. These properties are believed to result from a combination of fine particle size, normally about 40 microns and typically ranging from 20 to 60 microns. These fine particles from the centrifuge tend to agglomerate in the dryer resulting in an agglomerate particle size distribution having less than 3.2% less than 100 micron, about 21% between 200 and 300 microns, about 14% between 300 and 400 microns and about 59% greater than 400 microns. The average particle size, therefore, increases form less than 100 microns prior to the dryer to more than 100 microns after the dryer. The amount of attached biomass in the product is less than 1% by weight, and preferably within the range of from about 0.2 to 0.8 wt %. The remaining impurities in the final product sulfur are small amounts of sodium and sulfates.

In order to achieve this purity, and also to help prevent the entrance of undesired materials into the reactor, the water used in reslurrying should be free of materials which will attach to the sulfur. Preferably the water has been demineralized. Boiler feed water free of any treatment chemicals is suitable for this. The high solid cake removed from each of the two centrifuges of the process should contain at least 50 wt % solids, and preferably 60 wt % solids. The reslurrying step should result in a slurry containing less than 15 wt % solids with about 10% being preferred.

Biological conversion reactions differ from reactions promoted through the use of a classical catalyst in that operating conditions such as temperatures cannot be used in the same manner to increase reaction rates. The rate at which the biological organism converts the sulfur compound is governed by biological limits and is not controlled by reaction kinetics and thermodynamics as in a classical catalytic reactor. Performance may be influenced to some degree by operating temperature and by the relative abundance or lack of abundance of certain compounds in the reaction medium, but reaction rates are not adjustable in the same manner or to the same degree as with catalytic reactions. Therefore, it is necessary to optimize the process flow, the reactor size and the configuration of the overall process to adjust and control the biological conditions with the health and longevity of the bacteria in mind. Attention must therefore focus closely on such factors as overall reactor retention time, and adequate admixing of the contents of the reactor(s) such that localized concentrations do not inhibit the progress of the desired reaction and that the operating conditions of nutrient supply, temperature, pH, etc., are such that the growth and functioning of the biological agent is maximized. A suitable reaction zone should advance these objectives by allowing the removal of hydrogen sulfide, providing good admixture of the reactants and feed, and by providing means to adjust the concentration of nutrients and the pH of the reaction zone in a manner which will promote or maximize the conversion of the thiophenes.

The primary concern in the choice of operating conditions for the biological reaction zone is the health and longevity of the bacteria present in the zone. The biological reaction zone will preferably be operated at a pressure close to atmospheric. Operating conditions suitable for the biological reaction zone of the subject process include a temperature of about 20 to 100 degrees C., preferably 35 to 70 degrees C., and a positive pressure less than about 2 atmospheres. The biological process can often be run at ambient conditions in moderate and warm climates. As mentioned, the type of bacteria and the nature of the reaction will set many operating conditions and the required additives, such as the need for an electron donor or oxygen. An oxygen source such as air is added to an aerobic reaction zone and hydrogen or ethanol is typically added to an anaerobic zone as an electron donor or nutrient.

The composition of the feed stream(s) to the scrubbing zone can vary widely and does not control use of the process. The feed stream may be a gas such as a hydrogen rich gas stream or a natural gas stream. The feed may contain only a single hydrocarbonaceous compound, but is much more likely to be a mixture of a very large number of compounds as normally found in petroleum derived hydrocarbon fractions. A feed stream may contain several different organic sulfur compounds such as mercaptans and organic sulfides in addition to or instead of hydrogen sulfide. A liquid phase feed stream can comprise compounds boiling in the gasoline or (naphtha) boiling point range. Such feed streams will contain a mixture of hydrocarbon types such as a mixture of normal, branched chain, and cyclic paraffins plus alkylaromatics. The process is also readily applicable to lighter fractions such as LPG (liquefied petroleum gas). LPG is a mixture of light paraffinic hydrocarbons including propane and butane which are gaseous at standard conditions. The sulfur compound(s) converted in the reactor may be derived from hydrocarbon conversion units or from units which remove sulfur compounds or convert sulfur compounds such as a Claus unit. The sulfur compounds can also be derived from other treating units or scrubbing zones and may be in a form such as sulfites or sulfates which allows their direct passage into the reaction zone. Sulfur compounds from two or more sources may be charged to the same bioreaction zone.

The reactor is preferably maintained at basic conditions by the addition of a suitable aqueous alkaline solution. This is a small makeup stream as the reactor is expected to regenerate at least a majority of the hydroxyl ions used in the feed stream treating step. The aqueous alkaline solution present in the process can contain carbonate, phosphate, hydroxide or bicarbonate basic anions. The preferred basic aqueous solution comprises a bicarbonate solution. Stronger solutions of an alkaline metal hydroxide such as 1 to 40 wt. % sodium hydroxide, commonly referred to in the petroleum refining art as "caustic" could be used but are not preferred as they tend to damage or kill the presently preferred bacteria. The use of stronger bases in the reactor will require extensive measures such as dilution to preserve the bacteria. A preferred aqueous additive solution is a bicarbonate solution adjusted to a pH of about 9.0 as by the addition of a small amount of sodium hydroxide or potassium hydroxide. The amount of basic liquid, or if needed acidic liquid, added to the reactor should be controlled by an automated system monitoring the pH of the aqueous material present in the reactor. The pH may range from about 6.0 to about 12 and is preferably below 10.5. The basic anion of the solution is added to the solution in the form of alkali metal or ammonium compound or other water soluble compound. Examples of compounds which can be employed to produce the basic aqueous solution include sodium carbonate, sodium bicarbonate, sodium phosphate, potassium phosphate, and potassium carbonate. Two or more compounds can be employed. The aqueous solution used in the subject process preferably has a low concentration of the basic anion, preferably in the range of from about 0.02 to 1.0 wt. percent.

It may be necessary to charge one or more nutrients to the reaction zone. The nutrients may be added as solids or as an aqueous stream, which is another reason for the removal of a bleed stream by line 17 of the drawing. The nutrients will supply basic minerals required to sustain life such as potassium, phosphorous, magnesium, and nitrogen. The nutrients and the techniques for the addition of nutrients employed in the process may be those customarily employed in other reactors of a similar type.

A bioreactor design known in the art may be employed. A reactor similar to that illustrated in previously cited U.S. Pat. No. 5,637,220 is suitable and preferred. Bacteria known in the art may also be employed, with the use of naturally occurring members of the genus Thiobacillus being preferred. Further information on the operation of the bioreaction zones may be obtained from the previously cited references and from U.S. Pat. Nos. 5,565,098; 5,518,618; and 5,474,682 which are incorporated herein for their teaching on the construction and operation of bioreaction zones. Properly selected centrifuges and dryers of conventional construction may also be used. Some dryers are unsuitable due to the high moisture content and nature of the recovered sulfur. The dryers are preferably of a type described as a rotary dryer having a paddle driver. Steam is used for indirect heating. Such dryers are available through Hosokawa/Bepex.

What is claimed:

1. A biological process for conversion of sulfur compounds to elemental sulfur and the recovery of a hydrophilic fine particle sulfur product, which process comprises:

(a) passing an aqueous stream containing a sulfur compound into a biological reaction zone in which the sulfur compound is brought into contact with a bacteria at conversion promoting conditions under which the bacteria extracts sulfur from the sulfur compound, thereby forming elemental sulfur;

(b) removing a reactor effluent stream comprising water, biomass, particles of elemental sulfur and salts from the biological conversion zone and passing the reactor effluent stream into a separation zone in which water and biomass are separated from the reactor effluent stream to yield a separator effluent stream comprising particulate elemental sulfur and water;

(c) passing the separator effluent stream into a first centrifugal separation zone and removing water to yield a second separation zone effluent stream containing over about 50 wt % particulate elemental sulfur having attached biomass;

(d) admixing the second separation zone effluent stream with water to form a slurry containing less than about 15 wt % solids;

(e) passing the slurry into a second centrifugal separation zone and removing water to yield a third separation zone effluent stream containing over 50 wt % particulate elemental sulfur having attached biomass; and, (f) drying the third separation zone effluent stream to yield a hydrophilic fine particle elemental sulfur which contains attached biomass.

2. The process of claim 1 further characterized in that the hydrophilic fine particle sulfur contains less than about 0.75 wt % attached biomass.

3. The process of claim 1 further characterized in that the hydrophilic fine particle sulfur contains about 0.2 to about 0.75 wt % attached biomass.

4. The process of claim 1 further characterized in that the hydrophilic fine particle sulfur has an average particle size between about 20 and 60 microns.

5. The process of claim 1 further characterized in that the reaction zone is run at aerobic conditions.

6. The process of claim 5 further characterized in that the sulfur compound in the aqueous stream is a sulfide.

* * * * *